United States Patent
Soni (10) Patent No.: US 10,219,818 B2
(45) Date of Patent: Mar. 5, 2019

(54) SHAFT-BASED SURGICAL FORCEPS AND METHOD OF MANUFACTURING THE SAME

(71) Applicant: COVIDIEN LP, Mansfield, MA (US)

(72) Inventor: Purvish Soni, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 726 days.

(21) Appl. No.: 14/808,227

(22) Filed: Jul. 24, 2015

(65) Prior Publication Data
US 2017/0020543 A1 Jan. 26, 2017

(51) Int. Cl.
| | |
|---|---|
| A61B 18/14 | (2006.01) |
| A61B 17/29 | (2006.01) |
| A61B 17/00 | (2006.01) |
| A61B 18/00 | (2006.01) |

(52) U.S. Cl.
CPC .... *A61B 17/29* (2013.01); *A61B 2017/00477* (2013.01); *A61B 2017/00526* (2013.01); *A61B 2017/2902* (2013.01); *A61B 2017/2936* (2013.01); *A61B 2018/00589* (2013.01); *A61B 2018/1455* (2013.01)

(58) Field of Classification Search
CPC .... A61B 2017/2901; A61B 2017/2902; A61B 2017/2915; A61B 2017/2916; A61B 2017/2919; A61B 2017/2936; A61B 18/1447

See application file for complete search history.

(56) References Cited

U.S. PATENT DOCUMENTS

| | | | | |
|---|---|---|---|---|
| 5,201,743 | A | * 4/1993 | Haber | A61B 17/0469 606/146 |
| 5,358,506 | A | * 10/1994 | Green | A61B 17/29 227/181.1 |
| 5,605,272 | A | 2/1997 | Witt et al. | |
| 5,891,142 | A | 4/1999 | Eggers et al. | |
| 5,919,206 | A | 7/1999 | Gengler et al. | |
| 5,935,126 | A | 8/1999 | Riza | |
| 6,077,287 | A | 6/2000 | Taylor et al. | |

(Continued)

FOREIGN PATENT DOCUMENTS

| | | |
|---|---|---|
| EP | 2659849 A2 | 11/2013 |
| EP | 2659849 A3 | 1/2014 |

OTHER PUBLICATIONS

European Search Report issued in corresponding application No. 16180768.0 dated Nov. 14, 2016.

*Primary Examiner* — Jaymi Della
*Assistant Examiner* — Sean W Collins (57) ABSTRACT

A surgical instrument includes a shaft defining a proximal end, a distal end, an interior surface, and an exterior surface. The shaft includes a pair of channels defined in the interior surface thereof towards the distal end of the shaft. A drive member is movably disposed within the shaft. An end effector assembly is pivotably coupled to the shaft towards the distal end of the shaft. A cam pin operably couples the end effector assembly and the drive member such that movement of the drive member relative to the shaft manipulates the end effector assembly. Ends of the cam pin extend outwardly from the end effector assembly and are received within the channels of the shaft to guide movement of the cam pin relative to the shaft in response to movement of the drive member relative to the shaft.

11 Claims, 5 Drawing Sheets

(56) References Cited

U.S. PATENT DOCUMENTS

| | | |
|---|---|---|
| 6,129,740 A | 10/2000 | Michelson |
| 6,322,579 B1 | 11/2001 | Muller |
| 6,334,860 B1 | 1/2002 | Dorn |
| 6,443,968 B1 | 9/2002 | Holthaus et al. |
| 6,506,208 B2 | 1/2003 | Hunt et al. |
| 6,706,056 B2 | 3/2004 | Bacher |
| 6,716,232 B1 * | 4/2004 | Vidal ............... A61B 17/07207 227/176.1 |
| 6,770,072 B1 | 8/2004 | Truckai et al. |
| 6,790,217 B2 | 9/2004 | Schulze et al. |
| 6,887,240 B1 | 5/2005 | Lands et al. |
| 7,052,496 B2 | 5/2006 | Yamauchi |
| 7,147,638 B2 | 12/2006 | Chapman et al. |
| 7,150,097 B2 | 12/2006 | Sremcich et al. |
| 7,384,420 B2 | 6/2008 | Dycus et al. |
| 7,494,501 B2 | 2/2009 | Ahlberg et al. |
| 7,549,988 B2 | 6/2009 | Eberl et al. |
| 7,559,940 B2 | 7/2009 | McGuire et al. |
| 7,753,909 B2 | 7/2010 | Chapman et al. |
| 7,758,608 B2 | 7/2010 | DiCesare et al. |
| 7,766,910 B2 | 8/2010 | Hixson et al. |
| 7,877,853 B2 | 2/2011 | Unger et al. |
| 7,922,953 B2 | 4/2011 | Guerra |
| 8,241,320 B2 | 8/2012 | Lyons et al. |
| 8,252,021 B2 | 8/2012 | Boulnois et al. |
| 8,266,783 B2 | 9/2012 | Brandt et al. |
| 8,388,646 B2 | 3/2013 | Chojin |
| 8,394,094 B2 | 3/2013 | Edwards et al. |
| 8,409,244 B2 | 4/2013 | Hinman et al. |
| 8,545,534 B2 | 10/2013 | Ahlberg et al. |
| 8,551,090 B2 | 10/2013 | Sutter et al. |
| 8,728,118 B2 | 5/2014 | Hinman et al. |
| 8,740,933 B2 | 6/2014 | Anderson |
| 8,789,741 B2 | 7/2014 | Baxter, III et al. |
| 8,814,856 B2 | 8/2014 | Elmouelhi et al. |
| 8,858,553 B2 | 10/2014 | Chojin |
| 2003/0233109 A1 * | 12/2003 | Green ............... A61B 17/0057 606/144 |
| 2010/0042142 A1 * | 2/2010 | Cunningham ......... A61B 17/29 606/207 |
| 2011/0270251 A1 | 11/2011 | Horner et al. |
| 2011/0301592 A1 * | 12/2011 | Kerr ...................... A61B 17/29 606/41 |
| 2013/0138102 A1 * | 5/2013 | Twomey ............ A61B 18/1445 606/45 |
| 2014/0025070 A1 * | 1/2014 | Kerr .................... A61B 18/1445 606/45 |
| 2014/0025073 A1 | 1/2014 | Twomey et al. |
| 2014/0330308 A1 | 11/2014 | Hart et al. |
| 2016/0175001 A1 * | 6/2016 | Hibner ............. A61B 17/32009 606/28 |

* cited by examiner

SHAFT-BASED SURGICAL FORCEPS AND METHOD OF MANUFACTURING THE SAME

BACKGROUND

Technical Field

The present disclosure relates to surgical instruments and, more particularly, to shaft-based surgical forceps and methods of manufacturing shaft-based surgical forceps.

Background of Related Art

A forceps or hemostat is a plier-like instrument which relies on mechanical action between its jaws to grasp, clamp, and constrict tissue. Energy-based forceps utilize both mechanical clamping action and energy, e.g., electrosurgical energy, ultrasonic energy, light energy, microwave energy, heat, etc., to affect hemostasis by heating tissue to treat, e.g., coagulate, cauterize, and/or seal, tissue.

Shaft-based forceps typically employ a shaft having a handle at a proximal end thereof and a pair of jaw members at a distal end thereof. A drive assembly extending through the shaft operably couples the handle with the jaw members such that actuation of the handle moves one or both of the jaw members relative to the other to grasp tissue therebetween.

As the dimensions of shaft-based forceps are minimized, the sizes of the components disposed therein are also minimized, requiring that these components be capable of withstanding greater tolerances. Thus, there is presented a design challenge of providing a suitably small shaft-based forceps while reducing the tolerances of the components disposed therein to acceptable levels.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical instrument provided in accordance with aspects of the present disclosure includes a shaft defining a proximal end, a distal end, an interior surface, and an exterior surface. The shaft includes a pair of channels defined in the interior surface thereof towards the distal end of the shaft. A drive member is movably disposed within the shaft and an end effector assembly is pivotably coupled to the shaft towards the distal end of the shaft. A cam pin operably couples the end effector assembly and the drive member such that movement of the drive member relative to the shaft manipulates the end effector assembly. Ends of the cam pin extend outwardly from the end effector assembly and are received within the channels of the shaft to guide movement of the cam pin relative to the shaft in response to movement of the drive member relative to the shaft.

In an aspect of the present disclosure, the channels of the shaft are formed via embossed features raised in relief from the exterior surface of the shaft.

In another aspect of the present disclosure, each channel defines an angled section and a longitudinal section. The ends of the cam pin are moved through the longitudinal sections of the channels in response to movement of the drive member relative to the shaft. The angled sections of the channels may be used to facilitate assembly, as detailed below.

In yet another aspect of the present disclosure, the ends of the cam pin are configured for insertion into the angled sections of the channels and translation therealong to the longitudinal sections of the channels.

In still another aspect of the present disclosure, the end effector assembly includes first and second jaw members each defining at least one cam slot. The cam pin is configured for insertion through the least one cam slot of each of the first and second jaw members and translation therealong to move the first and second jaw members between a spaced-apart position and an approximated position in response to movement of the drive member relative to the shaft.

In still yet another aspect of the present disclosure, the first and second jaw members each define at least one pivot aperture. A pivot pin extends through the at least one pivot aperture of each of the first and second jaw members to pivotably couple the first and second jaw members to one another.

In another aspect of the present disclosure, a clevis extends distally from the distal end of the shaft and includes a pair of spaced-apart clevis members. Each clevis member defines an aperture. The pivot pin is further configured to extend through the apertures of the clevis members to pivotably couple the first and second jaw members to the shaft.

In still another aspect of the present disclosure, the drive member defines an aperture towards a distal end thereof. The aperture of the drive member is configured to receive the cam pin such that movement of the drive member relative to the shaft correspondingly moves the cam pin relative to the shaft.

In yet another aspect of the present disclosure, each of the first and second jaw members includes at least one proximal flange and a distal body. The at least one proximal flange of each of the jaw members defines the corresponding at least one cam slot therethrough.

In another aspect of the present disclosure, the distal body of each of the first and second jaw members include an electrically-conductive plate. The electrically-conductive plates are configured to grasp tissue therebetween in the approximated position of the first and second jaw members and adapted to connect to a source of energy for treating tissue grasped therebetween.

In still yet another aspect of the present disclosure, the instrument further includes a housing engaging the proximal end of the shaft, a drive assembly disposed within the housing and operably coupled to the drive member, and a handle assembly operably coupled to the housing and the drive assembly. The handle assembly includes a movable handle movable between a first position and a second position relative to the housing to move the drive member relative to the shaft.

A method of manufacturing a surgical instrument provided in accordance with aspects of the present disclosure includes coupling a cam pin with an end effector assembly and a drive member to operably couple the end effector assembly and the drive assembly to one another. The cam pin is positioned such that ends of the cam pin extend outwardly from the end effector assembly. The method further includes sliding the ends of the cam pin into channels defined within a shaft towards a distal end of the shaft to operably couple the end effector assembly and the drive member with the shaft. The channels retain the cam pin coupled to the end effector assembly and the drive member.

In an aspect of the present disclosure, the end effector assembly includes first and second jaw members and the method further includes inserting a pivot pin through the first and second jaw members to pivotably couple the first and second jaw members to one another.

In another aspect of the present disclosure, the first and second jaw members are pivotably coupled to one another prior to sliding the ends of the cam pin into the channels. In such aspects, the method further includes pivotably coupling ends of the pivot pin to the shaft.

In another aspect of the present disclosure, the method further includes, after sliding the ends of the cam pin into the channels, inserting the pivot pin through apertures defined within the shaft and the first and second jaw members to pivotably couple the first and second jaw members to one another and the shaft.

In yet another aspect of the present disclosure, sliding the ends of the cam pin into the channels includes inserting the ends of the cam pin into angled sections of the channels, sliding the ends of the cam pin through the angled sections of the channels, and sliding the ends of the cam pin into longitudinal sections of the channels.

In still another aspect of the present disclosure, the method further includes coupling the drive member to a drive assembly. Coupling the drive member to the drive assembly retains the ends of the cam pin with the longitudinal sections of the channels.

Another method of manufacturing a surgical instrument provided in accordance with aspects of the present disclosure includes inserting a cam pin through cam slots defined within first and second jaw members to operably couple the first and second jaw members to one another, such that ends of the cam pin extend outwardly from the first and second jaw members. The method further includes inserting the ends of the cam pin into angled sections of channels defined within a shaft, sliding the ends of the cam pin through the angled sections of the channels and into longitudinal sections of the channels, and inserting a pivot pin through apertures defined within the first and second jaw members and apertures defined within the shaft to pivotably couple the first and second jaw members to one another and the shaft.

In an aspect of the present disclosure, the method further includes inserting the cam pin through an aperture defined within a drive member to operably couple the first and second jaw members to the drive member.

In another aspect of the present disclosure, inserting the pivot pin through apertures defined within the first and second jaw members is performed before inserting the cam pin, and inserting the pivot pin through the apertures defined within the shaft is performed after inserting the cam pin.

BRIEF DESCRIPTION OF THE DRAWINGS

Various aspects and features of the present disclosure described herein with reference to the drawings wherein.

DETAILED DESCRIPTION

Figure 1:
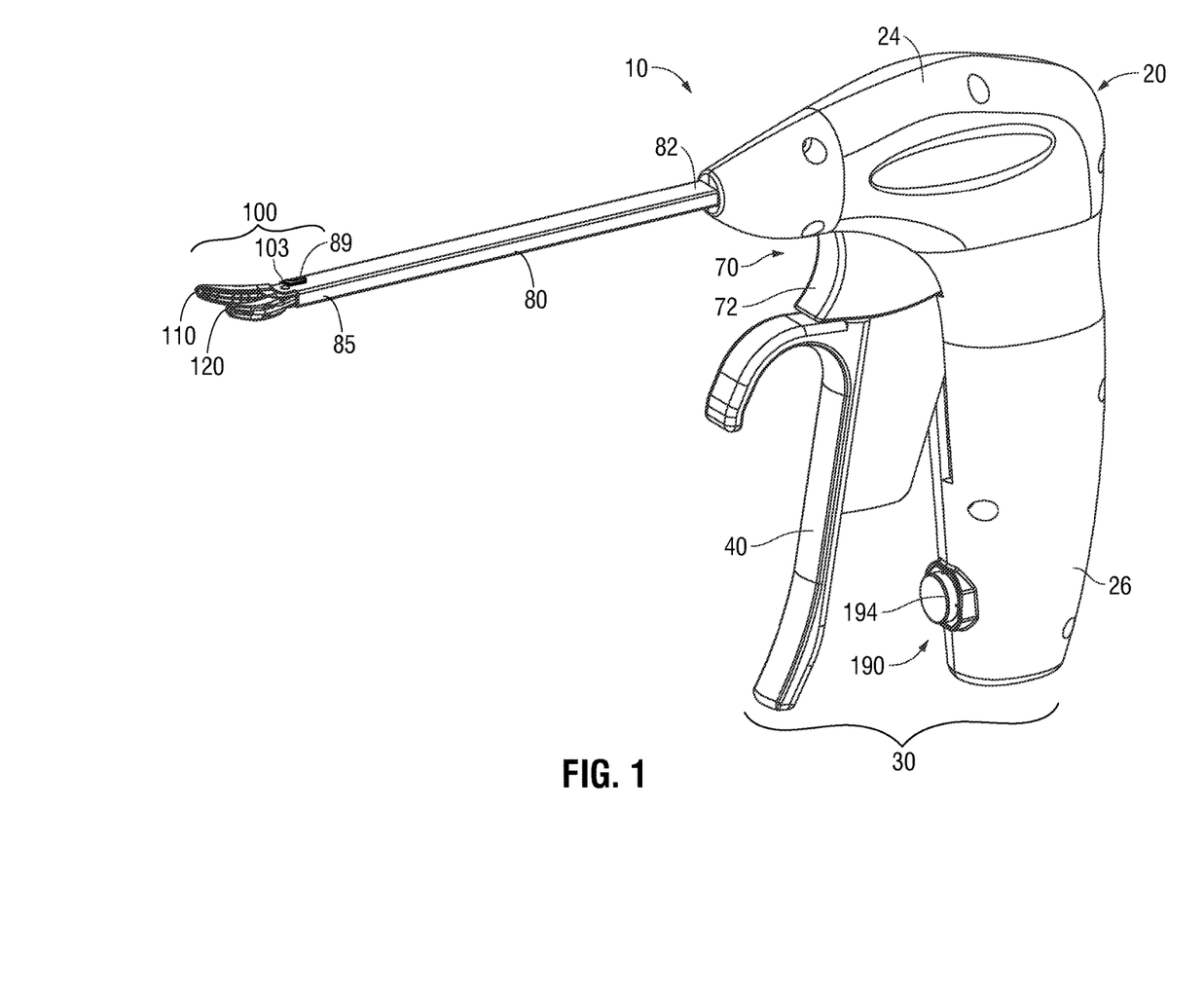
FIG. 1 is a perspective view of a shaft-based surgical forceps provided in accordance with the present disclosure with jaw members of the end effector assembly thereof disposed in a spaced-apart position.
Figure 2:
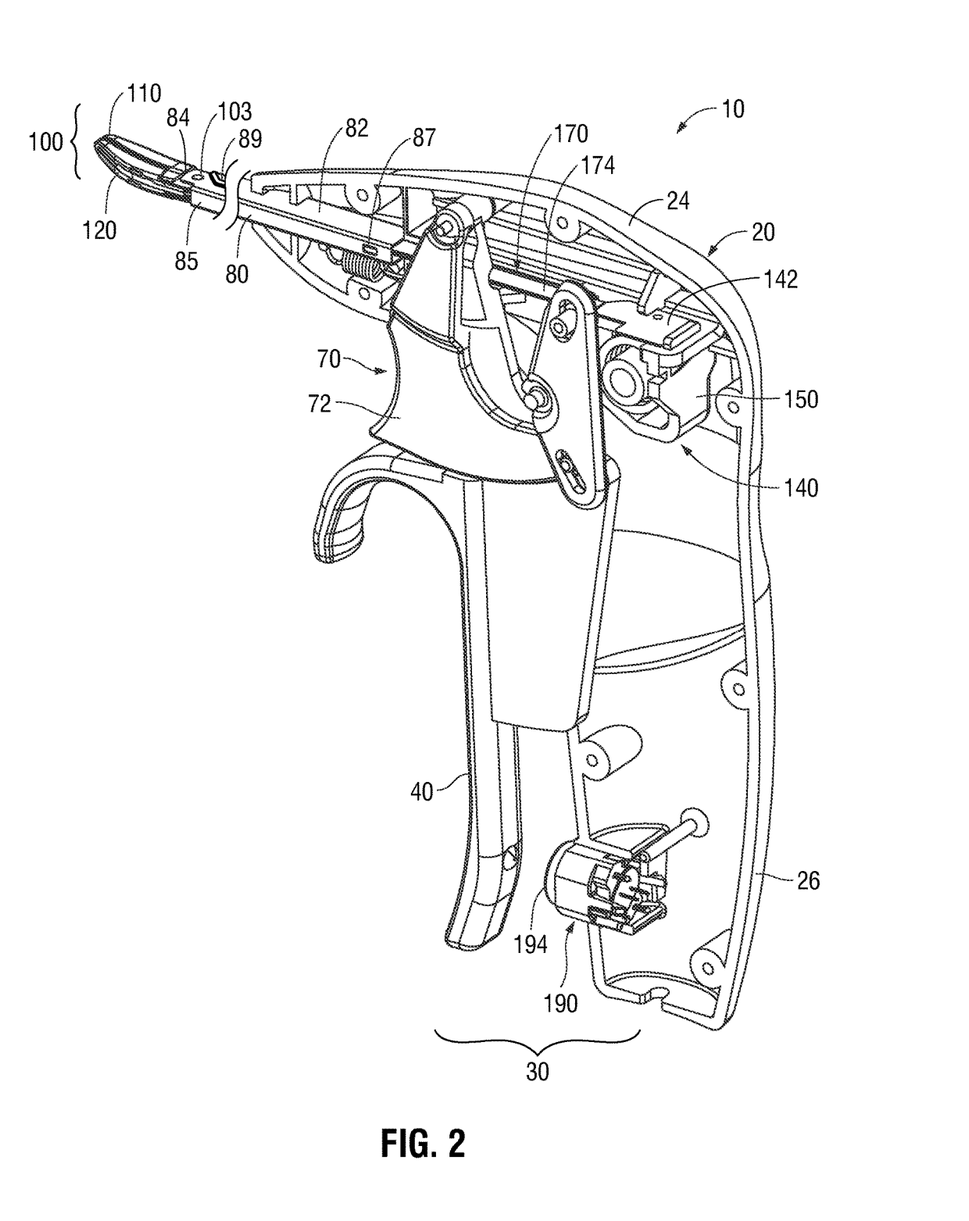
FIG. 2 is a rear, perspective view of the forceps of FIG. 1 with the jaw members disposed in the approximated position and a portion of the housing removed to illustrate the internal components thereof.
Figure 3:
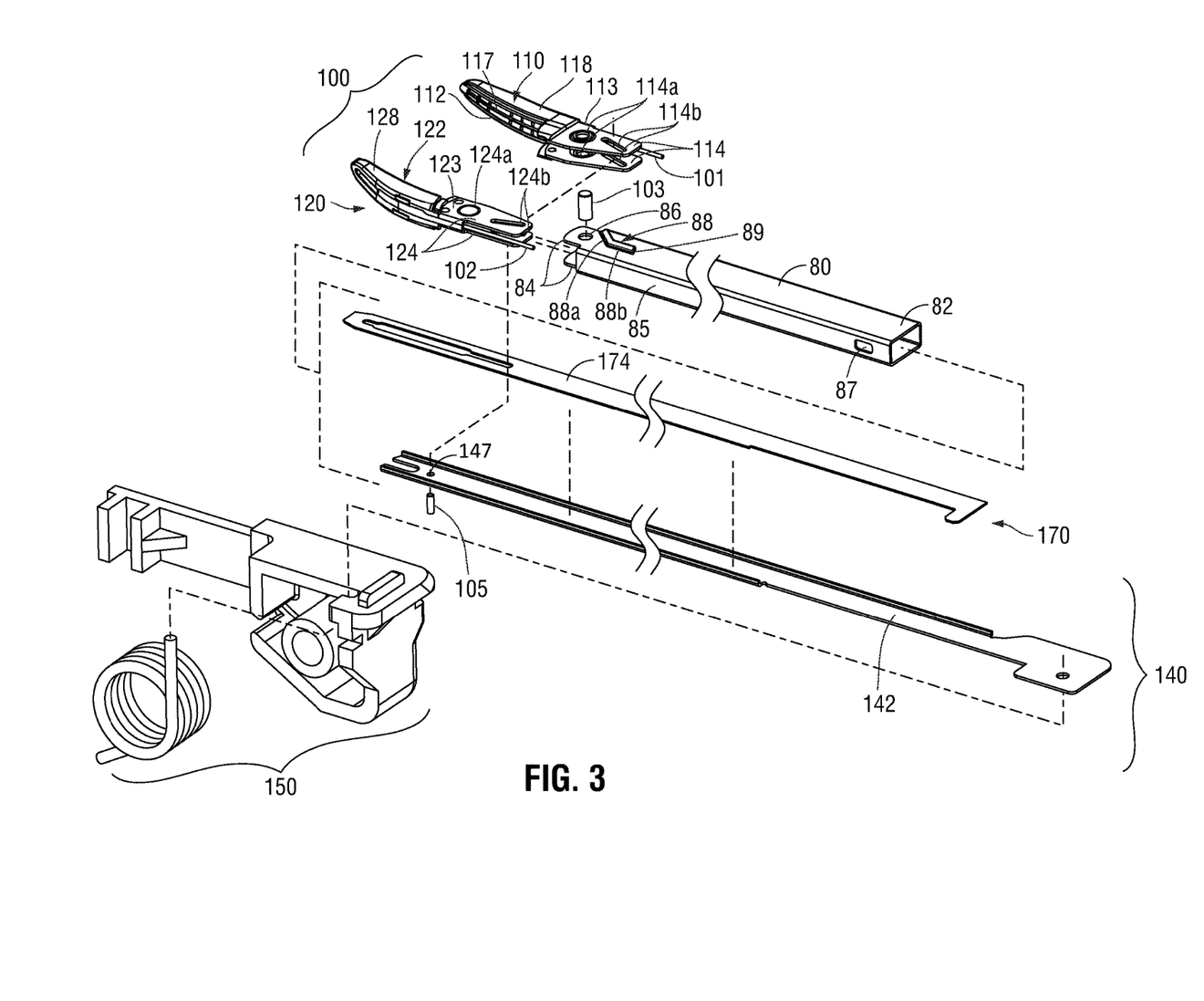
FIG. 3 is an enlarged, rear, perspective, exploded view of the drive assembly, shaft, and end effector assembly of the forceps of FIG. 1.

Referring generally to FIGS. 1-3, a shaft-based surgical forceps provided in accordance with the present disclosure is shown generally identified by reference numeral 10. Although detailed below with respect to forceps 10, the aspects and features of the present disclosure are equally applicable for use with any suitable shaft-based surgical instrument.

Forceps 10 is configured for grasping, treating, and/or dissecting tissue and generally includes a housing 20, a handle assembly 30, a trigger assembly 70, a shaft 80, an end effector assembly 100, a drive assembly 140, a knife assembly 170, and an energy activation assembly 190. As detailed below, shaft 80 extends distally from housing 20 and supports end effector assembly 100 at the distal end thereof; drive assembly 140 operably couples handle assembly 30 with end effector assembly 100 to enable selective manipulation of jaw members 110, 120 of end effector assembly 100 via actuation of movable handle 40 of handle assembly 30; knife assembly 170 is operably coupled with trigger assembly 70 to enable selective translation of a knife 174 of knife assembly 170 relative to end effector assembly 100; and energy activation assembly 190 enables energy to be selectively delivered to end effector assembly 100.

Forceps 10 may also include an electrosurgical cable (not shown) that connects forceps 10 to a generator (not shown) or other suitable power source, although forceps 10 may alternatively be configured as a battery-powered instrument. The electrosurgical cable includes lead wires, e.g., lead wires 101, 102 (FIG. 6), extending therethrough that have sufficient length to extend through housing 20 and shaft 80 in order to operably couple the generator, energy activation assembly 190, and end effector assembly 100 with one another to enable the selective supply of energy to jaw members 110, 120 of end effector assembly 100, e.g., upon activation of activation switch 194 of energy activation assembly 190.

Continuing with reference to FIGS. 1-3, housing 20 of forceps 10 houses the internal working components of forceps 10 and defines a pistol-style configuration having a longitudinally-extending barrel portion 24 and a fixed handle portion 26 that extends from barrel portion 24 in generally perpendicular orientation relative thereto. Activation switch 194 of energy activation assembly 190 is mounted on fixed handle portion 26 of housing 20 such that activation switch 194 may be activated by movable handle 40 upon sufficient movement of movable handle 40 towards fixed handle portion 26 of housing 20, as detailed below. Upon activation of activation switch 194, energy is supplied from the generator (not shown) to jaw members 110, 120 of end effector assembly 100 via lead wires 101, 102 (FIG. 6), respectively.

Shaft 80 extends distally from housing 20 and defines a generally rectangular cross-sectional configuration oriented such that the larger width dimension thereof extends laterally and the smaller height dimension thereof extends vertically. However, shaft 80 may alternatively define a square, polygonal, oval, or circular cross-sectional configuration and/or may define a different orientation. As described in greater detail below, shaft 80 includes a pair of spaced-apart clevis members 84 extending distally from the top and bottom walls, e.g., the larger width dimension walls, of shaft 80 at distal end 85 thereof, each of which defines an aperture 86 for receiving a pivot pin 103 to operably support end effector assembly 100 at distal end 85 of shaft 80. Shaft 80 also includes, at proximal end 82 thereof, a pair of engagement apertures 87 configured to receive engagement features (not shown) extending inwardly from housing 20 to secure proximal end 82 of shaft 80 within housing 20.

Figure 4:
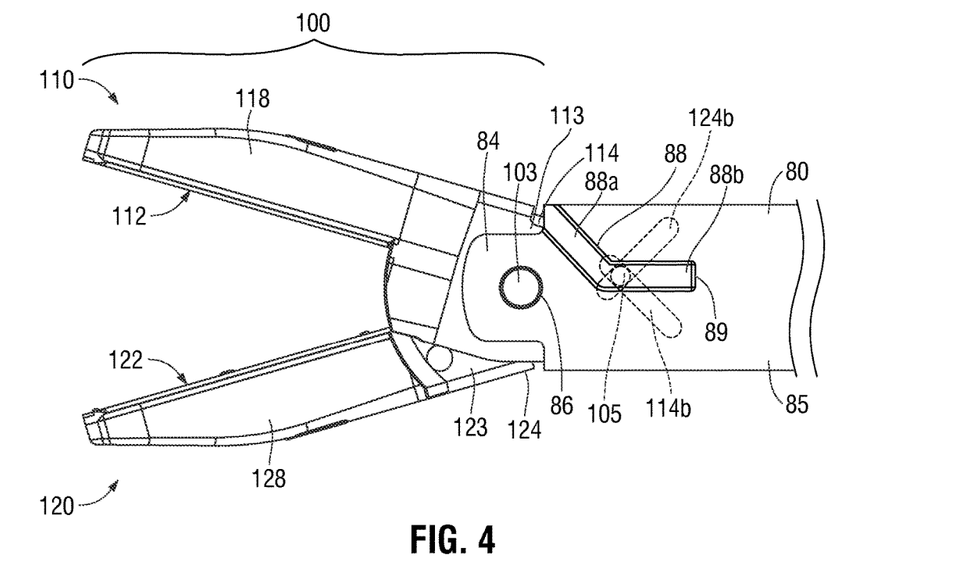
FIG. 4 is a side view of the distal end of the forceps of FIG. 1 with the jaw members disposed in the spaced-apart position.
Figure 5:
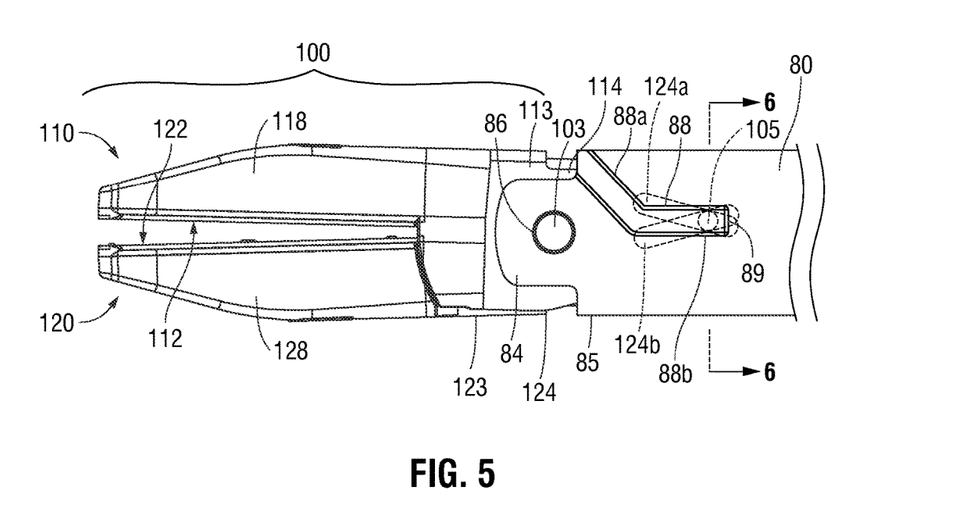
FIG. 5 is a side view of the distal end of the forceps of FIG. 1 with the jaw members disposed in the approximated position.
Figure 6:
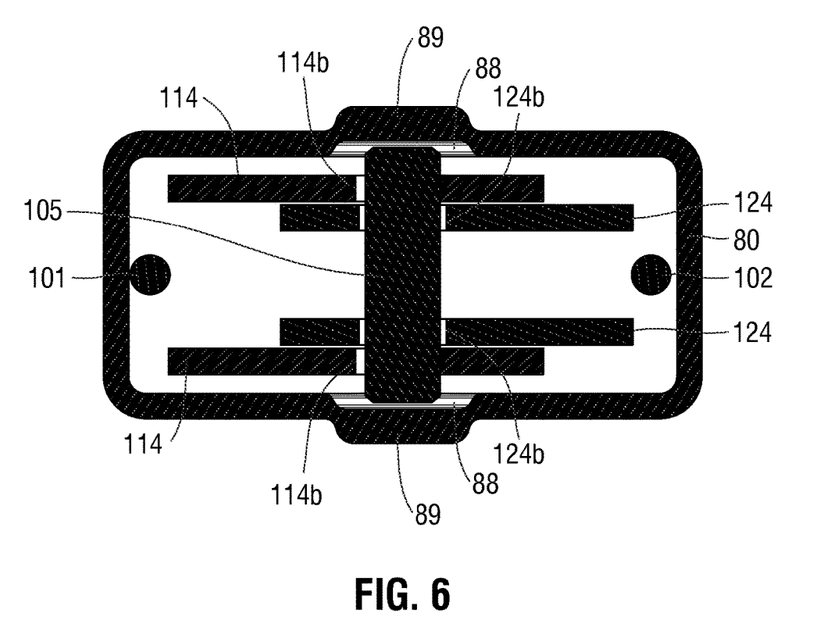
FIG. 6 is transverse, cross-sectional view of the distal end of the forceps of FIG. 1 taken across section line "6-6" of FIG. 5.

With additional reference to FIGS. 4-6, shaft 80 further includes a pair channels 88 define within the interior surfaces of the top and bottom walls, e.g., the larger width dimension walls, of shaft 80. Channels 88 may be formed via embossed features 89 that are raised in relief from the exterior surfaces of the top and bottom walls of shaft 80, thereby defining channels 88 on the opposite, interior surfaces of the top and bottom walls. Embossed features 89 may be formed via stamping or other suitable process and are configured such that channels 88 each define an angled portion 88a and a longitudinal portion 88b. Angled portions 88a of channels 88 are at least partially open to the distal end 85 of shaft 80 to enable slidable insertion of the ends of cam pin 105 of end effector assembly 100 into angled portions 88a of channels 88. Once the ends of cam pin 105 have been inserted into angled portions 88a of channels 88, cam pin 105 may be translated along angled portions 88a of channels 88 such that the ends thereof are translated through angled portions 88a and into longitudinal portions 88b of channels 88. Longitudinal portions 88b of channels 88 define lengths equal to or greater than the length of travel of cam pin 105 during movement of jaw members 110, 120 between the spaced-apart and approximated positions (FIGS. 4 and 5, respectively). The assembly and operable coupling of end effector assembly 100 with shaft 80 and drive assembly 140 via cam pin 105 is detailed below.

Referring again to FIGS. 1-3, handle assembly 30 includes a movable handle 40 that is movable relative to fixed handle portion 26 of housing 20 between an initial position and an activated position. Drive assembly 140 is operably coupled between movable handle 40 and end effector assembly 100 such that movement of movable handle 40 relative to fixed handle portion 26 of housing 20 between the initial position and the activated position imparts movement of jaw members 110, 120 of end effector assembly 100 between a spaced-apart position (FIG. 4) and an approximated position (FIG. 5) for grasping tissue therebetween. Further, in the activated position of movable handle 40, movable handle 40 is urged into contact with activation switch 194 of energy activation assembly 190 to activate activation switch 194 and thereby initiate the supply of energy from the generator (not shown) to end effector assembly 100 for treating grasped tissue.

Drive assembly 140 includes a drive plate 142 and a slider assembly 150. Drive plate 142 extends distally from housing 20 and through shaft 80 to operably engage end effector assembly 100. More specifically, a cam-pin aperture 147 configured to receive cam pin 105 of end effector assembly 100 is defined transversely through drive plate 142 towards the distal end of drive plate 142. Slider assembly 150 operably couples movable handle 40 with drive plate 142. As a result of this configuration, movement of movable handle 40 between the initial position and the activated position translates drive plate 142 through shaft 80 and, thus, translates cam pin 105 relative to end effector assembly 100 to pivot jaw members 110, 120 of end effector assembly 100 between the spaced-apart and approximated positions (FIGS. 4 and 5, respectively). A more detailed description of slider assembly 150 and other suitable slider assemblies configured for use with drive plate 142 can be found in U.S. patent application Ser. Nos. 14/719,422; 14/719,434; 14/719,452; 14/719,464; and Ser. No. 14/719,475, each of which was filed on May 22, 2105 and is incorporated by reference herein in its entirety.

Knife assembly 170 includes a knife 174 that is coupled to trigger assembly 70 such that actuation of trigger 72 of trigger assembly 70 advances knife 174 between jaw members 110, 120 of end effector assembly 100 to cut tissue grasped therebetween. A more detailed description of knife assembly 170 and trigger assembly 70 can be found in U.S. patent application Ser. Nos. 14/719,422; 14/719,434; 14/719,452; 14/719,464; and Ser. No. 14/719,475, previously incorporated by reference herein.

With reference to FIGS. 3-6, as mentioned above, end effector assembly 100 is operably supported at distal end 85 of shaft 80 and includes opposing jaw members 110, 120 pivotably coupled to one another and movable relative to one another shaft 80 between a spaced-apart position (FIG. 4) and an approximated position (FIG. 5) for grasping tissue therebetween. Each jaw member 110, 120 includes an electrically-conductive plate 112, 122, a jaw frame 113, 123, a spacer (not shown), and an outer housing 118, 128. Jaw members 110, 120 define curved configurations, wherein jaw members 110, 120 bend upwardly from a longitudinal axis of shaft 80, e.g., towards the upper, larger width dimension wall of shaft 80, although linear jaw members or jaw members curved in a different direction may alternatively be provided.

Jaw frames 113, 123 of jaw members 110, 120 each include a pair of spaced-apart proximal flanges 114, 124 and a distal jaw support (not shown). The distal jaw supports of jaw frames 113, 123 support electrically-conductive plates 112, 122, the spacers (not shown), and outer housings 118, 128 of the respective jaw members 110, 120 thereon. Electrically-conductive plates 112, 122 are electrically connected to energy activation assembly 190 (FIGS. 1 and 2) via leads 101, 102, respectively, and are electrically-isolated from jaw frames 113, 123 via outer housings 118, 128 and/or the spacers (not shown).

Continuing with reference to FIGS. 3-6, proximal flanges 114 of jaw member 110 are spaced-apart further than proximal flanges 124 of jaw member 120 so as to allow proximal flanges 124 of jaw member 120 to be positioned between proximal flanges 114 of jaw member 110 during assembly, although proximal flanges 114, 124 of jaw members 110, 120, respectively, may alternatively be configured for positioning in an offset, overlapping configuration relative to one another. Each pair of proximal flanges 114, 124 defines an aligned pivot aperture 114a, 124a and an aligned cam slot 114b, 124b. Pivot pin 103 of end effector assembly 100 is configured for insertion through apertures 86 of clevis members 84 of shaft 80 and pivot apertures 114a, 124a to pivotably couple jaw members 110, 120 to shaft 80 and one another to enable jaw members 110, 120 to pivot laterally, e.g., along the larger width dimension of shaft 80, between the spaced-apart and approximated positions (FIGS. 4 and 5, respectively). Pivot pin 103 and/or proximal flanges 114, 124 of jaw members 110, 120 may include features (not shown) or otherwise be configured to retain pivot pin 103 in engagement within pivot apertures 114a, 124a of proximal flanges 114, 124 of jaw members 110, 120, e.g., to inhibit pivot pin 103 from transversely sliding out of engagement with proximal flanges 114, 124, as detailed below.

Cam slots 114b of proximal flanges 114 of jaw member 110 are oppositely angled relative to cam slots 124b of proximal flanges 124 of jaw member 120. Cam pin 105 of end effector assembly 100 is configured for insertion through cam slots 114b, 124b of proximal flanges 114, 124 of jaw members 110, 120, as well as cam-pin aperture 147 of drive plate 142 to operable couple drive plate 142 with jaw members 110, 120. As a result of this configuration, and with cam slots 114b of proximal flanges 114 oppositely angled relative to cam slots 124b of proximal flanges 124, translation of drive plate 142 relative to jaw members 110, 120 translates cam pin 105 through cam slots 114b, 124b to pivot jaw members 110, 120 about pivot pin 103 and relative to one another and shaft 80 between the spaced-apart and approximated positions (FIGS. 4 and 5, respectively).

The free ends of cam pin 105, which extend outwardly from proximal flanges 114 of jaw members 110, 120 when inserted through jaw members 110, 120 and drive plate 142, are configured for receipt within longitudinal sections 88b of channels 88 of shaft 80, as noted above. Longitudinal sections 88b of channels 88 of shaft 80 inhibit cam pin 105 from transversely sliding out of engagement with cam slots 114b, 124b of proximal flanges 114, 124 of jaw members 110, 120 and cam-pin aperture 147 of drive plate 142. Longitudinal sections 88b of channels 88 also guide the longitudinal translation of cam pin 105 relative to shaft 80 during longitudinal translation of drive plate 142 through shaft 80 to pivot jaw members 110, 120 between the spaced-apart and approximated positions (FIGS. 4 and 5, respectively).

Referring generally to FIGS. 1-6, the assembly of end effector assembly 100 and the coupling of the assembled end effector assembly 100 with shaft 80 and drive plate 142 are described. Initially, to assembly end effector assembly 100, jaw members 110, 120 are manipulated such that proximal flanges 124 of jaw member 120 are disposed between proximal flanges 114 of jaw member 110 with the pairs of pivot apertures 114a, 124a of proximal flanges 114, 124 of jaw members 110, 120, respectively, aligned with each other. Once this position has been achieved, pivot pin 103 is inserted through the pivot aperture 114a of one of the proximal flanges 114 of jaw member 110, the pivot apertures 124a of the proximal flanges 124 of jaw member 120, and the pivot aperture 114a of the other proximal flange 114 of jaw member 110 such that the ends of pivot pin 103 extend outwardly from each of the proximal flanges 114 of jaw member 110.

As noted above, pivot pin 103 and/or proximal flanges 114, 124 of jaw members 110, 120 may include features (not shown) or otherwise be configured to retain pivot pin 103 within pivot apertures 114a, 124a. More specifically, once pivot pin 103 is inserted through pivot apertures 114a, 124a as detailed above, pivot pin 103 may be welded to the portions of the outwardly-facing surfaces of proximal flanges 114 surrounding pivot apertures 114a of jaw member 110, or may otherwise be engaged therewith to the inhibit transverse sliding of pivot pin 103 relative to jaw member 110. Regardless of the configuration, in this assembled state end effector assembly 100, pivot pin 103 is operably retained in position with the ends of pivot pin 103 extending outwardly from each proximal flange 114 of jaw member 110.

Once end effector assembly 100 has been assembled, e.g., as detailed above, end effector assembly 100 may be coupled with shaft 80 and drive plate 142. That is, jaw members 110, 120 may initially be coupled to one another to form end effector assembly 100, followed by the assembled end effector assembly 100 being coupled with shaft 80 and drive plate 142. In order to couple the assembled end effector assembly 100 with shaft 80 and drive plate 142, cam pin 105 is inserted through the cam slot 114b of one of the proximal flanges 114 of jaw member 110, the cam slot 124b of one of the proximal flanges 124 of jaw member 120, cam-pin aperture 147 of drive plate 142, the cam slot 124b of the other proximal flange 124 of jaw member 120, and the cam slot 114b of the other proximal flange 114 of jaw member 110 such that the ends of cam pin 105 extend outwardly from each of the proximal flanges 114 of jaw member 110.

With cam pin 105 inserted through proximal flanges 114 of jaw member 110, proximal flanges 124 of jaw member 120, and drive plate 142, as detailed above, drive plate 142 is operably coupled to cam pin 105 such that translation of drive plate 142 through shaft 80 and relative to end effector assembly 100 translates cam pin 105 through cam slots 114b, 124b of jaw members 110, 120, respectively.

Once insertion of cam pin 105, as detailed above, has been accomplished, end effector assembly 100 may be coupled to distal end 85 of shaft 80. In order to couple end effector assembly 100 to distal end 85 of shaft 80, the ends of cam pin 105 which extend outwardly from jaw members 110, 120 are guided into the open distal ends of angled portions 88a of channels 88 at the distal end 85 of shaft 80 and are slid proximally along angled portions 88a of channels 88 into longitudinal portions 88b of channels 88.

With the ends of cam pin 105 positioned within longitudinal portions 88b of channels 88, cam pin 105 is retained in position extending through proximal flanges 114 of jaw member 110, proximal flanges 124 of jaw member 120, and drive plate 142 and is restricted to longitudinal movement relative to shaft 80, despite being "floating," that is, without otherwise being engaged with shaft 80, jaw members 110, 120, or drive plate 142 other than the fact that cam pin 105 extends through cam slots 114b, 124b, cam-pin aperture 147, and has its ends disposed within channels 88. Upon coupling of drive plate 142 with slider assembly 150, the distal-most position of drive plate 142 relative to shaft 80, e.g., corresponding to the initial position of movable handle 40, is defined such that cam pin 105 is inhibited from sliding distally into angled sections 88a of channels 88 and, thus, is retained within longitudinal sections 88a of channels 88. As noted above, longitudinal sections 88a of channels 88 define lengths equal to or greater than the length of travel of cam pin 105 during movement of jaw members 110, 120 between the spaced-apart and approximated positions (FIGS. 4 and 5, respectively) such that cam pin 105 need only travel within longitudinal sections 88a of channels 88 and such that longitudinal sections 88a of channels 88 permit full pivoting of jaw members 110, 120 between the spaced-apart and approximated positions (FIGS. 4 and 5, respectively).

During or after sliding the ends of cam pin 105 into channels 88 to operably retain cam pin 105 therebetween, the ends of pivot pin 103 are inserted into apertures 86 of spaced-apart clevis members 84 to pivotably couple jaw members 110, 120 with shaft 80 and to retain jaw members 110, 120 at distal end 85 of shaft 80. This may be accomplished by flexing clevis members 84 apart from one another to permit the ends of pivot pin 103 to slide along the inner surfaces of clevis members 84 and into alignment with apertures 86. Upon achieving this alignment, clevis members 84 are released or return back to their original position such that the ends of pivot pin 103 are urged through apertures 86 to pivotably retain pivot pin 103 between clevis members 84.

As an alternatively to retaining pivot pin 103 in engagement with jaw members 110, 120 and subsequently coupling the ends of pivot pin 103 to clevis members 84, as detailed above, the insertion of pivot pin 103 may be withheld until the end of the above-detailed assembly. That is, in such embodiments, jaw members 110, 120 and drive plate 142 may be coupled to one another and shaft 80 via the insertion of cam pin 105 through proximal flanges 114, 124 and drive plate 142 and sliding insertion of the ends of cam pin 105 into channels 88 of shaft 80, similarly as detailed above. Thereafter, with the pairs of pivot apertures 114a, 124a of proximal flanges 114, 124 of jaw members 110, 120, respectively, aligned with each other and apertures 86 of clevis members 84, pivot pin 103 may be inserted through pivot apertures 114a, 124a and apertures 86. Pivot pin 103 may be operably retained in position once inserted in this manner via any suitable feature or in any other suitable fashion, e.g., via welding the ends of pivot pin 103 to clevis members 84, rivets formed on the ends of pivot pin 103 that extend outwardly from clevis members 84, etc.

At any suitable point during the above-detailed assembly, lead wires 101, 102 (FIG. 6) may be routed from jaw members 110, 120 through shaft 80 and into housing 20, ultimately to be electrically coupled to energy activation assembly 190 and/or the electrosurgical cable (not shown) to enable connection to the generator (not shown).

Referring still to FIGS. 1-6, the use and operation of forceps 10 is described. Initially, movable handle 40 is disposed in the initial position, drive plate 142 is disposed in a distal-most position to maintain cam pin 105 at the distal ends of cam slots 114b, 124b and at the distal end of longitudinal sections 88b of channels 88 of shaft 80, and, correspondingly, jaw members 110, 120 are disposed in the spaced-apart position (FIG. 4). Trigger 72 is initially is disposed in the un-actuated position and, accordingly, knife 174 is disposed in a retracted position, wherein knife 174 is disposed between proximal flanges 114, 124 of jaw members 110, 120 but does not extend distally therefrom so as to avoid interference with tissue disposed between jaw members 110, 120.

In order to move jaw members 110, 120 to the approximated position to grasp tissue therebetween, movable handle 40 is pulled proximally towards fixed handle portion 26 from the initial position towards the activation position. Upon such movement of movable handle 40, slider assembly 150 is translated proximally through housing 20, thereby pulling drive plate 142 proximally. As drive plate 142 is pulled proximally, cam pin 105 is pulled proximally through cam slots 114b, 124b of jaw members 110, 120 and longitudinal sections 88b of channels 88 of shaft 80 such that jaw members 110, 120 are pivoted from the spaced-apart position (FIG. 4) towards the approximated position (FIG. 5) to grasp tissue therebetween. As noted above, longitudinal section 88b of channels 88 of shaft 80 guide translation of cam pin 105 as cam pin 105 is pulled through cam slots 114b, 124b and ensure that cam pin 105 is translated longitudinally. This configuration reduces the tolerances on cam pin 105 and, thus, enables use of a cam pin 105 having a relatively shorter length as compared to a cam pin that does not have its ends seated within channels 88. As can be appreciated, a shorter cam pin 105 allows for a smaller-diameter shaft, which is advantageous for use in endoscopic procedures and in other procedures with significant spatial constraints.

In order to apply energy to tissue grasped between jaw members 110, 120 to treat tissue, movable handle 40 is moved further towards fixed handle portion 26 to the activation position, wherein an appropriate closure force or closure force within an appropriate range, is achieved, as described in detail in U.S. patent application Ser. Nos. 14/719,422; 14/719,434; 14/719,452; 14/719,464; and Ser. No. 14/719,475, previously incorporated by reference herein. Further, in the activation position of movable handle 40, energy activation is initiated. More specifically, in the activation position, movable handle 40 contacts switch 194 sufficiently so as to depress and activate switch 194. Switch 194, as noted above, is disposed in electrical communication with the generator (not shown) and electrically-conductive plates 112, 122 of jaw members 110, 120, respectively, such that activation of switch 194 initiates the supply of energy to electrically-conductive plates 112, 122 to treat, e.g., coagulate, cauterize, and/or seal, tissue grasped therebetween.

Once tissue has been treated or where it is only desired to cut tissue, knife 174 may be advanced between jaw members 110, 120 to cut tissue grasped therebetween. In order to advance knife 174 from the retracted position to an extended position, trigger 72 is pulled proximally from an un-actuated position to an actuated position. As trigger 72 is pulled proximally, trigger assembly 70 cooperates with knife assembly 170, as detailed in U.S. patent application Ser. Nos. 14/719,422; 14/719,434; 14/719,452; 14/719,464; and Ser. No. 14/719,475, previously incorporated by reference herein, to advance knife 174 distally. As knife 174 is advanced distally, knife 174 enters knife slots 117 (only the knife slot of jaw member 110 is shown) defined within electrically-conductive plates 112, 122 of jaw members 110, 120, respectively, and translates therethrough to the extended position to divide tissue grasped between jaw members 110, 120.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a shaft defining a proximal end, a distal end, an interior surface, and an exterior surface, the shaft including a pair of channels defined in the interior surface thereof towards the distal end of the shaft, each channel having a closed exteriorly-facing side and an open interiorly-facing side;
   a drive member movably disposed within the shaft;
   an end effector assembly pivotably coupled to the shaft towards the distal end of the shaft; and
   a cam pin operably coupling the end effector assembly and the drive member such that movement of the drive member relative to the shaft manipulates the end effector assembly, wherein ends of the cam pin extend outwardly from the end effector assembly and are received within the pair of channels of the shaft, and wherein the pair of channels are configured to guide movement of the cam pin therethrough and relative to the shaft in response to movement of the drive member relative to the shaft, wherein each channel of the pair of channels extends to a distal edge of the distal end of the shaft and is at least partially open to the distal edge of the distal end of the shaft to enable slidable insertion of the ends the cam pin into the pair of channels.

2. The surgical instrument according to claim 1, wherein the shaft includes a pair of embossed features raised in relief from opposite sides of the exterior surface of the shaft, the pair of channels defined in the respective pair of embossed features.

3. The surgical instrument according to claim 1, wherein each channel defines an angled section and a longitudinal section, and wherein the ends of the cam pin are moved through the longitudinal sections of the pair of channels in response to movement of the drive member relative to the shaft.

4. The surgical instrument according to claim 3, wherein the ends of the cam pin are configured for insertion into the angled sections of the pair of channels and translation therealong to the longitudinal sections of the pair of channels.

5. The surgical instrument according to claim 1, wherein the end effector assembly includes first and second jaw members each defining at least one cam slot, the cam pin configured for insertion through the least one cam slot of each of the first and second jaw members and translation therealong to move the first and second jaw members between a spaced-apart position and an approximated position in response to movement of the drive member relative to the shaft.

6. The surgical instrument according to claim 5, wherein the first and second jaw members each define at least one pivot aperture and wherein a pivot pin extends through the at least one pivot aperture of each of the first and second jaw members to pivotably couple the first and second jaw members to one another.

7. The surgical instrument according to claim 6, further including a clevis extending distally from the distal end of the shaft, the clevis including a pair of spaced-apart clevis members each defining an aperture, wherein the pivot pin is further configured to extend through the apertures of the clevis members to pivotably couple the first and second jaw members to the shaft.

8. The surgical instrument according to claim 5, wherein the drive member defines an aperture towards a distal end thereof, the aperture of the drive member configured to receive the cam pin such that movement of the drive member relative to the shaft correspondingly moves the cam pin relative to the shaft.

9. The surgical instrument according to claim 5, wherein each of the first and second jaw members includes at least one proximal flange and a distal body, the at least one proximal flange defining the at least one cam slot therethrough.

10. The surgical instrument according to claim 9, wherein the distal body of each of the first and second jaw members includes an electrically-conductive plate, the electrically-conductive plates configured to grasp tissue therebetween in the approximated position of the first and second jaw members and adapted to connect to a source of energy for treating the tissue grasped therebetween.

11. The surgical instrument according to claim 1, further including:
    a housing engaging the proximal end of the shaft;
    a drive assembly disposed within the housing and operably coupled to the drive member; and
    a handle assembly operably coupled to the housing and the drive assembly, the handle assembly including a movable handle movable between a first position and a second position relative to the housing to move the drive member relative to the shaft.

* * * * *